US011788131B2

United States Patent
Ng et al.

(10) Patent No.: US 11,788,131 B2
(45) Date of Patent: Oct. 17, 2023

(54) METHODS OF IDENTIFYING COMBINATIONS OF TRANSCRIPTION FACTORS

(71) Applicant: President and Fellows of Harvard College, Cambridge, MA (US)

(72) Inventors: Hon Man Alex Ng, Cambridge, MA (US); George M. Church, Cambridge, MA (US); Parastoo Khoshakhlagh, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 350 days.

(21) Appl. No.: 17/045,474

(22) PCT Filed: Apr. 5, 2019

(86) PCT No.: PCT/US2019/025986
§ 371 (c)(1),
(2) Date: Oct. 5, 2020

(87) PCT Pub. No.: WO2019/195675
PCT Pub. Date: Oct. 10, 2019

(65) Prior Publication Data
US 2021/0054448 A1 Feb. 25, 2021

Related U.S. Application Data

(60) Provisional application No. 62/653,576, filed on Apr. 6, 2018.

(51) Int. Cl.
*C12Q 1/6869* (2018.01)
*C12Q 1/6876* (2018.01)

(52) U.S. Cl.
CPC ......... *C12Q 1/6869* (2013.01); *C12Q 1/6876* (2013.01); *C12Q 2525/143* (2013.01); *C12Q 2525/204* (2013.01); *C12Q 2563/185* (2013.01); *C12Y 207/07* (2013.01)

(58) Field of Classification Search
None
See application file for complete search history.

(56) References Cited

U.S. PATENT DOCUMENTS

| 7,812,124 | B2 | 10/2010 | Palm |
| 9,057,053 | B2 | 6/2015 | Wernig et al. |
| 9,273,119 | B2 | 3/2016 | Maizels et al. |
| 9,487,757 | B2 | 11/2016 | Tesar et al. |

(Continued)

FOREIGN PATENT DOCUMENTS

| CN | 102796696 A | 11/2012 |
| EP | 3118306 A1 | 1/2017 |

(Continued)

OTHER PUBLICATIONS

International Search Report and Written Opinion dated Jul. 15, 2019 for Application No. PCT/US2019/0259866.

(Continued)

*Primary Examiner* — Samuel C Woolwine
(74) *Attorney, Agent, or Firm* — Wolf, Greenfield & Sacks, P.C.

(57) ABSTRACT

Provided herein, in some embodiments, are methods and compositions for identifying combinations of transcription factors, for example, those involved in cell type conversion processes, such as cell differentiation.

36 Claims, 4 Drawing Sheets
Specification includes a Sequence Listing.

(56) References Cited

U.S. PATENT DOCUMENTS

| | | |
|---|---|---|
| 9,732,128 B2 | 8/2017 | West et al. |
| 2003/0092009 A1 | 5/2003 | Palm |
| 2004/0219575 A1 | 11/2004 | Neuman et al. |
| 2007/0161023 A1 | 7/2007 | Palm |
| 2009/0176724 A1 | 7/2009 | Shen et al. |
| 2010/0093092 A1 | 4/2010 | Bamdad et al. |
| 2011/0154518 A1 | 6/2011 | Kim et al. |
| 2012/0070419 A1 | 3/2012 | Christiansen-Weber |
| 2012/0107284 A1 | 5/2012 | Kozlova |
| 2012/0129262 A1 | 5/2012 | West et al. |
| 2012/0157474 A1 | 6/2012 | Dreyfuss et al. |
| 2012/0207744 A1 | 8/2012 | Mendlein et al. |
| 2013/0022583 A1 | 1/2013 | Wernig et al. |
| 2013/0029423 A1 | 1/2013 | Yamanaka et al. |
| 2013/0160152 A1 | 6/2013 | Ostertag et al. |
| 2013/0330825 A1 | 12/2013 | Couture et al. |
| 2014/0170752 A1 | 6/2014 | Pulst et al. |
| 2014/0234971 A1 | 8/2014 | Slukvin et al. |
| 2015/0044187 A1 | 2/2015 | Visel et al. |
| 2015/0284681 A1 | 10/2015 | Wernig et al. |
| 2016/0010056 A1 | 1/2016 | Nakaki et al. |
| 2016/0038544 A1 | 2/2016 | Keller et al. |
| 2016/0201053 A1 | 7/2016 | Maizels et al. |
| 2016/0237402 A1 | 8/2016 | Tilly et al. |
| 2017/0087192 A1 | 3/2017 | Tilly et al. |
| 2018/0127714 A1 | 5/2018 | Ko |
| 2018/0289748 A9 | 10/2018 | Tilly et al. |
| 2019/0017032 A1 | 1/2019 | Firas et al. |
| 2019/0233795 A1 | 8/2019 | Ng et al. |
| 2020/0063105 A1 | 2/2020 | Ng et al. |
| 2021/0171902 A1 | 6/2021 | Khoshakhlagh et al. |
| 2022/0204926 A1 | 6/2022 | Ng et al. |

FOREIGN PATENT DOCUMENTS

| | | |
|---|---|---|
| JP | 2021-040578 A | 3/2021 |
| WO | WO 2004/060302 A2 | 7/2004 |
| WO | WO 2006/005043 A2 | 1/2006 |
| WO | WO 2008/153568 A1 | 12/2008 |
| WO | WO 2009/029315 A2 | 3/2009 |
| WO | WO 2009/029315 A9 | 5/2009 |
| WO | WO 2009/137674 A2 | 11/2009 |
| WO | WO 2009/137844 A2 | 11/2009 |
| WO | WO 2011/091048 A1 | 7/2011 |
| WO | WO 2012/054896 A1 | 4/2012 |
| WO | WO 2013/124309 A1 | 8/2013 |
| WO | WO 2013/170146 A1 | 11/2013 |
| WO | WO 2015/049677 A1 | 4/2015 |
| WO | WO 2015/084908 A1 | 6/2015 |
| WO | WO 2016/012570 A1 | 1/2016 |
| WO | WO 2016/103269 A1 | 6/2016 |
| WO | WO 2016/120493 A1 | 8/2016 |
| WO | WO 2016/163958 A1 | 10/2016 |
| WO | WO 2017/015075 A1 | 1/2017 |
| WO | WO 2018/049382 A1 | 3/2018 |
| WO | WO 2018/204262 A1 | 11/2018 |
| WO | WO 2019/108894 A1 | 6/2019 |
| WO | WO 2020/243392 A1 | 12/2020 |
| WO | WO 2020/243643 A1 | 12/2020 |

OTHER PUBLICATIONS

International Preliminary Report on Patentability dated Oct. 15, 2020 for Application No. PCT/US2019/025986.

[No Author Listed], Genbank Submission; NIH/NCBI, Accession No. EF587698. Jul. 16, 2007. 2 pages.

[No Author Listed], Genbank Submission; NIH/NCBI, Accession No. NM_203289. Dec. 28, 2019. 4 pages.

[No Author Listed], Genbank Submission; NIH/NCBI, Accession No. EF687698. Dec. 8, 2016. 1 page.

[No Author Listed], Genbank Submission; NIH/NCBI, Accession No. NM_001173531. Dec. 28, 2019. 4 pages.

[No Author Listed], Genbank Submission; NIH/NCBI, Accession No. NM_001285986. Dec. 28, 2019. 4 pages.

[No Author Listed], Genbank Submission; NIH/NCBI, Accession No. NM_001285987. Dec. 28, 2019. 4 pages.

[No Author Listed], Genbank Submission; NIH/NCBI, Accession No. NM_002176. Dec. 31, 2019. 3 pages.

[No Author Listed], Genbank Submission; NIH/NCBI, Accession No. NM_002701. Dec. 31, 2019. 5 pages.

[No Author Listed], Genbank Submission; NIH/NCBI, Accession No. NM_005806. Sep. 27, 2019. 3 Pages.

[No Author Listed], Genbank Submission; NIH/NCBI, Accession No. NM_006168. Aug. 2, 2019. 3 pages.

[No Author Listed], Genbank Submission; NIH/NCBI, Accession No. NM_152568. Oct. 23, 2019. 3 pages.

[No Author Listed], Genbank Submission; NIH/NCBI, Accession No. NM_177400. Oct. 1, 2019. 3 pages.

[No Author Listed], Genbank Submission; NIH/NCBI, Accession No. Z46629. Oct. 7, 2008. 3 pages.

[No Author Listed], ORFeome Collaboration. The ORFeome Collaboration: a genome-scale human ORF-clone resource. Nat Methods. Mar. 2016;13(3):191-2. doi: 10.1038/nmeth.3776.

Adamson et al., A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.

Burdo et al., The Maize TFome—development of a transcription factor open reading frame collection for functional genomics. Plant J. Oct. 2014;80(2):356-66. doi: 10.1111/tpj.12623. Epub Aug. 26, 2014.

Busskamp et al., Rapid neurogenesis through transcriptional activation in human stem cells. Mol Syst Biol. Nov. 17, 2014;10:760(1-21). doi: 10.15252/msb.20145508.

Carstens, Identification and nucleotide sequence of the regions of Autographa californica nuclear polyhedrosis virus genome carrying insertion elements derived from Spodoptera frugiperda. Virology. Nov. 1987;161(1):8-17. doi: 10.1016/0042-6822(87)90165-6.

Chanda et al., Generation of induced neuronal cells by the single reprogramming factor ASCL1. Stem Cell Reports. Aug. 12, 2014;3(2):282-96. doi: 10.1016/j.stemcr.2014.05.020. Epub Jul. 4, 2014.

Chavez et al., Comparative analysis of Cas9 activators across multiple species. Nat Methods. Jul. 2016;13(7):563-567. doi: 10.1038/nmeth.3871. Epub May 23, 2016. Author Manuscript, 16 pages.

Chavez et al., Highly efficient Cas9-mediated transcriptional programming. Nat Methods. Apr. 2015;12(4):326-8. doi: 10.1038/nmeth.3312. Epub Mar. 2, 2015. Author Manuscript, 11 pages.

Chen et al., Inducing goat pluripotent stem cells with four transcription factor mRNAs that activate endogenous promoters. BMC Biotechnol. 2017;17(1):11(1-10). Published Feb. 13, 2017. doi:10.1186/s12896-017-0336-7.

Choi et al., A comparison of genetically matched cell lines reveals the equivalence of human iPSCs and ESCs. Nat Biotechnol. Nov. 2015;33(11):1173-81. doi: 10.1038/nbt.3388. Epub Oct. 26, 2015. Author Manuscript, 22 pages.

Darr et al., Overexpression of NANOG in human ES cells enables feeder-free growth while inducing primitive ectoderm features. Development. Mar. 2006;133(6):1193-201.

Dixit et al., Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.

Douvaras et al., Generation and isolation of oligodendrocyte progenitor cells from human pluripotent stem cells. Nat Protoc. Aug. 2015;10(8):1143-54. doi: 10.1038/nprot.2015.075. Epub Jul. 2, 2015.

Ehrlich et al., Rapid and efficient generation of oligodendrocytes from human induced pluripotent stem cells using transcription factors. Proc Natl Acad Sci U S A. Mar. 14, 2017;114(11):E2243-E2252. doi: 10.1073/pnas.1614412114. Epub Feb. 28, 2017.

Fraser et al., Acquisition of Host Cell DNA Sequences by Baculoviruses: Relationship Between Host DNA Insertions and FP Mutants of Autographa californica and Galleria mellonella Nuclear Polyhedrosis Viruses. J Virol. Aug. 1983;47(2):287-300. doi: 10.1128/JVI.47.2.287-300.1983.

(56) References Cited

OTHER PUBLICATIONS

Garcia-Leon et al., SOX10 Single Transcription Factor-Based Fast and Efficient Generation of Oligodendrocytes from Human Pluripotent Stem Cells. Stem Cell Reports. Feb. 13, 2018;10(2):655-672. doi: 10.1016/j.stemcr.2017.12.014. Epub Jan. 11, 2018.
Gohl et al., Large-scale mapping of transposable element insertion sites using digital encoding of sample identity. Genetics. Mar. 2014;196(3):615-23. doi: 10.1534/genetics.113.159483. Epub Dec. 27, 2013.
Goparaju et al., Rapid differentiation of human pluripotent stem cells into functional neurons by mRNAs encoding transcription factors. Sci Rep. Feb. 13, 2017;7:42367(1-12). doi: 10.1038/srep42367.
Gorbacheva et al., Improved transposon-based library preparation for the Ion Torrent platform. Biotechniques. Apr. 1, 2015;58(4):200-2. doi: 10.2144/000114277.
Gradwohl et al., neurogenin3 is required for the development of the four endocrine cell lineages of the pancreas. Proc Natl Acad Sci U S A. Feb. 15, 2000;97(4):1607-11.
Haenebalcke et al., The ROSA26-iPSC mouse: a conditional, inducible, and exchangeable resource for studying cellular (De)differentiation. Cell Rep. Feb. 21, 2013;3(2):335-41. doi: 10.1016/j.celrep.2013.01.016. Epub Feb. 7, 2013.
Hou et al., Sleeping Beauty transposon system for genetic etiological research and gene therapy of cancers. Cancer Biol Ther. 2015;16(1):8-16. doi: 10.4161/15384047.2014.986944.
Hsieh et al., PKCalpha expression regulated by Elk-1 and MZF-1 in human HCC cells. Biochem Biophys Res Commun. 2006;339(1):217-225. doi:10.1016/j.bbrc.2005.11.015.
Hui et al., Isolation and functional characterization of the human gene encoding the myeloid zinc finger protein MZF-1. Biochemistry. 1995;34(50):16493-16502. doi:10.1021/bi00050a033.
Ivics et al., Molecular reconstruction of Sleeping Beauty, a Tc1-like transposon from fish, and its transposition in human cells. Cell. Nov. 14, 1997;91(4):501-10. doi: 10.1016/s0092-8674(00)80436-5.
Jaitin et al., Dissecting Immune Circuits by Linking CRISPR-Pooled Screens with Single-Cell RNA-Seq. Cell. Dec. 15, 2016;167(7):1883-1896.e15. doi: 10.1016/j.cell.2016.11.039.
Kim et al., Oct4-induced oligodendrocyte progenitor cells enhance functional recovery in spinal cord injury model. Embo J. Oct. 23, 2015;34(23):2971-83.
Klein et al., Droplet barcoding for single-cell transcriptomics applied to embryonic stem cells. Cell. May 21, 2015;161(5):1187-1201 and Supplemental Info. doi: 10.1016/j.cell.2015.04.044.
Li et al., Neural Stem Cells Engineered to Express Three Therapeutic Factors Mediate Recovery from Chronic Stage CNS Autoimmunity. Mol Ther. Aug. 2016;24(8):1456-69. doi: 10.1038/mt.2016.104. Epub May 16, 2016.
Macosko et al., Highly Parallel Genome-wide Expression Profiling of Individual Cells Using Nanoliter Droplets. Cell. May 21, 2015;161(5):1202-1214. doi: 10.1016/j.cell.2015.05.002.
Morris et al., The myeloid zinc finger gene, MZF-1, regulates the CD34 promoter in vitro. Blood. 1995;86(10):3640-3647.
Mulvaney et al., Atoh1, an essential transcription factor in neurogenesis and intestinal and inner ear development: function, regulation, and context dependency. J Assoc Res Otolaryngol. Jun. 2012;13(3):281-93. doi: 10.1007/s10162-012-0317-4. Epub Feb. 28, 2012.
Najm et al., Transcription factor-mediated reprogramming of fibroblasts to expandable, myelinogenic oligodendrocyte progenitor cells. Nat Biotechnol. May 2013;31(5):426-33. doi: 10.1038/nbt.2561. Epub Apr. 14, 2013.
Ng, Differentiation of Human Cells and Tissues Using a Comprehensive Human Transcription Factor Library. Doctoral dissertation, Harvard University, Graduate School of Arts & Sciences. 2018. Retrieved from https://dash.harvard.edu/handle/1/41129209. 105 pages.
Nishiyama et al., Uncovering early response of gene regulatory networks in ESCs by systematic induction of transcription factors. Cell Stem Cell. Oct. 2, 2009;5(4):420-33. doi: 10.1016/j.stem.2009.07.012. Author Manuscript, 23 pages.
Pagliuca et al., Generation of functional human pancreatic β cells in vitro. Cell. Oct. 9, 2014;159(2):428-39. doi: 10.1016/j.cell.2014.09.040. Author Manuscript, 29 pages.
Pashai et al., Genome-wide profiling of pluripotent cells reveals a unique molecular signature of human embryonic germ cells. PLoS One. 2012;7(6):e39088(1-19). doi:10.1371/journal.pone.0039088.
Perrotti et al., Overexpression of the zinc finger protein MZF1 inhibits hematopoietic development from embryonic stem cells: correlation with negative regulation of CD34 and c-myb promoter activity. Mol Cell Biol. 1995;15(11):6075-6087. doi:10.1128/mcb.15.11.6075.
Rukstalis et al., Neurogenin3: a master regulator of pancreatic islet differentiation and regeneration. Islets. Nov.-Dec. 2009;1(3):177-84. doi: 10.4161/isl.1.3.9877.
Sagal et al., Proneural transcription factor Atoh1 drives highly efficient differentiation of human pluripotent stem cells into dopaminergic neurons. Stem Cells Transl Med. Aug. 2014;3(8):888-98. doi: 10.5966/sctm.2013-0213. Epub Jun. 5, 2014.
Selvaraj et al., Switching cell fate: the remarkable rise of induced pluripotent stem cells and lineage reprogramming technologies. Trends Biotechnol. Apr. 2010;28(4):214-23. doi: 10.1016/j.tibtech.2010.01.002. Epub Feb. 9, 2010.
Simicevic et al., Absolute quantification of transcription factors during cellular differentiation using multiplexed targeted proteomics. Nat Methods. Jun. 2013;10(6):570-6. doi: 10.1038/nmeth.2441. Epub Apr. 14, 2013.
Singari et al., Singari S, Javeed N, Tardi NJ, Marada S, Carlson JC, Kirk S, Thorn JM, Edwards KA. Inducible protein traps with dominant phenotypes for functional analysis of the *Drosophila* genome. Genetics. Jan. 2014;196(1):91-105. doi: 10.1534/genetics.113.157529. Epub Oct. 30, 2013.
Sripal, Combined expression of microRNAs and transcription factors for promoting hair cell differentiation. 2013 Master's Thesis. Department of Biomedical Sciences. Creighton University, 89 pages. Submitted Jul. 29, 2013.
Stolt et al., The Sox9 transcription factor determines glial fate choice in the developing spinal cord. Genes Dev. Jul. 1, 2003;17(13):1677-89.
Suchorska et al., Comparison of Four Protocols to Generate Chondrocyte-Like Cells from Human Induced Pluripotent Stem Cells (hiPSCs). Stem Cell Rev Rep. Apr. 2017;13(2):299-308. doi: 10.1007/s12015-016-9708-y.
Takahashi et al., Induction of pluripotent stem cells from mouse embryonic and adult fibroblast cultures by defined factors. Cell. Aug. 25, 2006;126(4):663-76. Epub Aug. 10, 2006.
Trounson, Pluripotent stem cells progressing to the clinic. Nat Rev Mol Cell Biol. Mar. 2016;17(3):194-200. doi: 10.1038/nrm.2016.10.
Van Der Maaten et al., Visualizing Data using t-SNE. J Mach Learn Res. 2008;9(86):2579-2605.
Vaquerizas et al., A census of human transcription factors: function, expression and evolution. Nat Rev Genet. Apr. 2009;10(4):252-63. doi: 10.1038/nrg2538.
Walczak et al., Directed differentiation of human iPSC into insulin producing cells is improved by induced expression of PDX1 and NKX6.1 factors in IPC progenitors. J Transl Med. Dec. 20, 2016;14(1):341. doi: 10.1186/s12967-016-1097-0.
Wang et al., Human iPSC-derived oligodendrocyte progenitor cells can myelinate and rescue a mouse model of congenital hypomyelination. Cell Stem Cell. Feb. 7, 2013;12(2):252-64. doi: 10.1016/j.stem.2012.12.002.
Williams et al., Snapshot: directed differentiation of pluripotent stem cells. Cell. May 25, 2012;149(5):1174-1174.e1. doi: 10.1016/j.cell.2012.05.015. 2 pages.
Yamakawa et al., Screening of Human cDNA Library Reveals Two differentiation-Related Genes, HHEX and HLX, as Promoters of Early Phase Reprogramming toward Pluripotency. Stem Cells. Nov. 2016;34(11):2661-2669. doi: 10.1002/stem.2436. Epub Jul. 8, 2016.
Yamamizu et al., Identification of transcription factors for lineage-specific ESC differentiation. Stem Cell Reports. Dec. 2013;1(6):545-59. doi: 10.1016/j.stemcr.2013.10.006. eCollection 2013.

(56) References Cited

OTHER PUBLICATIONS

Yamanaka, Induced pluripotent stem cells: past, present, and future. Cell Stem Cell. Jun. 14, 2012;10(6):678-684. doi: 10.1016/j.stem.2012.05.005.

Yang et al., Generation of oligodendroglial cells by direct lineage conversion. Nat Biotechnol. May 2013;31(5):434-9. doi: 10.1038/nbt.2564. Epub Apr. 14, 2013.

Zhang et al., Rapid single-step induction of functional neurons from human pluripotent stem cells. Neuron. Jun. 5, 2013;78(5):785-98. doi: 10.1016/j.neuron.2013.05.029. Author Manuscript, 24 pages.

[No Author Listed], Origene, Product datasheet for RC211285L1, BAPX1 (NKX3-2) (NM_001189) Human Tagged ORF Clone. Retrieved Nov. 15, 2022. https://www.origene.com/catalog/cdna-clones/expression-plasmids/rc211285l1/bapx1-nkx3-2-nm_001189-human-tagged-orf-clone.

Abed et al., Transplantation of macaca cynomolgus iPS-derived hematopoietic cells in NSG immunodeficient mice. Haematologica. Oct. 2015;100(10):e428-31. Epub Jun. 18, 2015.

Benabdellah et al., Development of an all-in-one lentiviral vector system based on the original TetR for the easy generation of Tet-ON cell lines. PLoS One. 2011;6(8):e23734. Epub Aug. 18, 2011.

Cao et al., Restoring BMP4 expression in vascular endothelial progenitors ameliorates maternal diabetes-induced apoptosis and neural tube defects. Cell Death Dis. Oct. 15, 2020;11(10):859.

Goldman et al., How to make an oligodendrocyte. Development. Dec. 1, 2015;142(23):3983-95. doi: 10.1242/dev.126409.

Ikuno et al., Correction: efficient and robust differentiation of endothelial cells from human induced pluripotent stem cells via lineage control with VEGF and cyclic AMP. PLoS One. Apr. 17, 2017;12(4):e0176238. Erratum for: PLoS One. Mar. 13, 2017;12(3):e0173271.

Kim et al., Selective depletion of SSEA-3- and TRA-1-60-Positive undifferentiated human embryonic stem cells by magnetic activated cell sorter (MACS). Tissue Eng. and Regen. Med. 2011;8(2):253-261.

Klum et al., Sequentially acting SOX proteins orchestrate astrocyte- and oligodendrocyte-specific gene expression. EMBO Rep. Nov. 2018;19(11):e46635. Epub Aug. 30, 2018.

Makar et al., Stem cell based delivery of IFN-beta reduces relapses in experimental autoimmune encephalomyelitis. J Neuroimmunol. May 30, 2008;196(1-2):67-81. doi: 10.1016/j.jneuroim.2008.02.014. Epub May 8, 2008.

Neman et al., A method for deriving homogenous population of oligodendrocytes from mouse embryonic stem cells. Dev Neurobiol. Jun. 2012;72(6):777-88. doi: 10.1002/dneu.22008.

Ng et al., A comprehensive library of human transcription factors for cell fate engineering. Nat Biotechnol. Apr. 2021;39(4):510-519. Epub Nov. 30, 2020. Author Manuscript, 37 pages.

Patsch et al., Generation of vascular endothelial and smooth muscle cells from human pluripotent stem cells. Nat Cell Biol. Aug. 2015;17(8):994-1003. Epub Jul. 27, 2015. Supplementary Information, 9 pages.

Rufaihah et al., Human induced pluripotent stem cell-derived endothelial cells exhibit functional heterogeneity. Am J Transl Res. 2013;5(1):21-35. Epub Jan. 21, 2013.

Sarkar et al., The sox family of transcription factors: versatile regulators of stem and progenitor cell fate. Cell Stem Cell. Jan. 3, 2013;12(1):15-30.

SEQUENCE LISTING

<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
aagtacgttg tttaggagtc                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
cggagtcatc ggagagagct                                          20

<210> SEQ ID NO 3
<211> LENGTH: 20

-continued

```
<212> TYPE: DNA
<213> ORGANISM: Artificial Sequence
<220> FEATURE:
<223> OTHER INFORMATION: Synthetic polynucleotide

<400> SEQUENCE: 3
gtttatggat caccctaggc                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
tagagcgtgg tcgtgaacat                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
accttactgt ggtaggtgac                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
agactagagg atgcccatca                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
tgagtaccag ttattagcgg                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
tgcactccag gtactgagtt                                                 20

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
```
gcgtgttcaa atggtatagg                                            20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
atactggata gccgatgttt                                            20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
cgtaccaata actcgaggca                                            20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
tggataggat gatggtgagc                                            20

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
ttgtgtcaga ttagacaagg                                            20

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
ccggtgaaga gggagtttgc                                            20

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
cagaccgtaa ggagactttg                                            20

<210> SEQ ID NO 16
<211> LENGTH: 20
<212> TYPE: DNA
<213> ORGANISM: Artificial Sequence -continued

```
<220> FEATURE:
<223> OTHER INFORMATION: Synthetic polynucleotide

<400> SEQUENCE: 16
aatggcaggc ctttgacatc                                          20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
tttcgaattc gttattctga                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
caaaggaggc ggtactgagc                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 19
tcgggtgcag agttcttata                                          20

<210> SEQ ID NO 20
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 20

Glu Gly Arg Gly Ser Leu Leu Thr Cys Gly Asp Val Glu Glu Asn Pro
1               5                   10                  15

Gly Pro

<210> SEQ ID NO 21
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 21

Ala Thr Asn Phe Ser Leu Leu Lys Gln Ala Gly Asp Val Glu Glu Asn
1               5                   10                  15

Pro Gly Pro

<210> SEQ ID NO 22
<211> LENGTH: 20
<212> TYPE: PRT
<213> ORGANISM: Artificial Sequence
<220> FEATURE:
```

-continued

```
<223> OTHER INFORMATION: Synthetic polypeptide

<400> SEQUENCE: 22

Gln Cys Thr Asn Tyr Ala Leu Leu Lys Leu Ala Gly Asp Val Glu Ser
1               5                   10                  15

Asn Pro Gly Pro
            20

<210> SEQ ID NO 23
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 23

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 24
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 24
aatgatacgg cgaccaccga gatctacact ctttccctac acgacgctc            49

<210> SEQ ID NO 25
<211> LENGTH: 86
<212> TYPE: DNA
<213> ORGANISM: Artificial Sequence
<220> FEATURE:
<223> OTHER INFORMATION: Synthetic polynucleotide

<400> SEQUENCE: 25
caagcagaag acggcatacg agatatgctg tcgtgactgg agttcagacg tgtgctcttc    60
cgatctccaa gcacctgcta catagc                                        86

<210> SEQ ID NO 26
<211> LENGTH: 86
<212> TYPE: DNA
<213> ORGANISM: Artificial Sequence
<220> FEATURE:
<223> OTHER INFORMATION: Synthetic polynucleotide

<400> SEQUENCE: 26
caagcagaag acggcatacg agattgtaca aagtgactgg agttcagacg tgtgctcttc    60
cgatctccaa gcacctgcta catagc                                        86

<210> SEQ ID NO 27
<211> LENGTH: 86
<212> TYPE: DNA
<213> ORGANISM: Artificial Sequence
<220> FEATURE:
<223> OTHER INFORMATION: Synthetic polynucleotide

<400> SEQUENCE: 27
caagcagaag acggcatacg agatcacggc ctgtgactgg agttcagacg tgtgctcttc    60
cgatctccaa gcacctgcta catagc                                        86
```

```
<210> SEQ ID NO 28
<211> LENGTH: 86
<212> TYPE: DNA
<213> ORGANISM: Artificial Sequence
<220> FEATURE:
<223> OTHER INFORMATION: Synthetic polynucleotide

<400> SEQUENCE: 28
caagcagaag acggcatacg agatgcatat gggtgactgg agttcagacg tgtgctcttc      60
cgatctccaa gcacctgcta catagc                                          86

<210> SEQ ID NO 29
<211> LENGTH: 86
<212> TYPE: DNA
<213> ORGANISM: Artificial Sequence
<220> FEATURE:
<223> OTHER INFORMATION: Synthetic polynucleotide

<400> SEQUENCE: 29
caagcagaag acggcatacg agattactcg ccgtgactgg agttcagacg tgtgctcttc      60
cgatctccaa gcacctgcta catagc                                          86

<210> SEQ ID NO 30
<211> LENGTH: 86
<212> TYPE: DNA
<213> ORGANISM: Artificial Sequence
<220> FEATURE:
<223> OTHER INFORMATION: Synthetic polynucleotide

<400> SEQUENCE: 30
caagcagaag acggcatacg agatatagaa gtgtgactgg agttcagacg tgtgctcttc      60
cgatctccaa gcacctgcta catagc                                          86

<210> SEQ ID NO 31
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 31
caagtttgta caaaaaagtt g                                               21

<210> SEQ ID NO 32
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 32
ccactttgta caagaaagtt g                                               21

<210> SEQ ID NO 33
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 33
caccaccacc accaccac                                                   18
```

```
<210> SEQ ID NO 34
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 34
ggggttgggg ttgcgccttt t                                                    21
```

METHODS OF IDENTIFYING COMBINATIONS OF TRANSCRIPTION FACTORS

RELATED APPLICATIONS

This application is a national stage filing under 35 U.S.C. § 371 of international application number PCT/US2019/025986, filed Apr. 5, 2019, which claims the benefit under 35 U.S.C. § 119(e) of U.S. provisional application No. 62/653,576, filed Apr. 6, 2018, each of which is herein incorporated by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 5, 2020, is named H049870671US01-SEQ-FL and is 7,909 bytes in size.

BACKGROUND

Cellular reprogramming plays a key role in the production of the various cell types needed for disease modeling, drug discovery, disease treatment and tissue engineering. As an example, stem cells can be differentiated into oligodendrocyte progenitor cells, myoblasts, neurons, cardiomyocytes, macrophages, hepatocytes, and blood progenitors for cell therapy. Although transcription factors are key regulators of cell identity, a single transcription factor is often not sufficient to induce cell differentiation. Instead a combination of transcription factors is usually required. Thus, there is a need to conduct large-scale overexpression analyses to identify transcription factor combinations in an unbiased manner.

SUMMARY

Provided herein, in some embodiments, are methods and nucleic acids for identifying transcription factor combinations for cellular reprogramming (e.g., stem cell differentiation). Although transcription factors are known modulators of cell identity, unbiased characterization of transcription factor combinations are limited, in part due to the lack of efficient methods for associating a transcription factor combination with a particular cellular phenotype (e.g., transcriptome). The experimental results provided herein, however, show unexpectedly that barcoded transposon expression vector (e.g., barcoded piggyBAC™ expression vector) of the present disclosure enables high resolution identification of transcription factor combinations driving a particular cell state, even in stem cells.

Accordingly, some aspects of the present disclosure provide a population of nucleic acids comprising a transposon carrying a cargo element that comprises a promoter operably linked to a sequence encoding a transcription factor and a barcode that is located within 100 nucleotides (e.g., 50 nucleotides) of a terminator sequence. In some embodiments, the transposon comprises terminal repeats (e.g., inverted terminal repeat sequences or long terminal repeat sequences) flanking the cargo element. In some embodiments, the terminal repeats are recognized by a transposase (e.g., a piggyBAC™ transposase). In some embodiments, the nucleic acids encode more than one transcription factor and one barcode that uniquely identifies the combination of transcription factors encoded by the nucleic acid.

Other aspects of the present disclosure provide a cloning vector that includes terminal repeats flanking a promoter operably linked to a multiple cloning site and a barcode that is located within 100 nucleotides (e.g., 50 nucleotides) of a terminator sequence. In some embodiments, the cloning vector is a piggyBAC™ cloning vector (i.e., a cloning vector that comprises piggyBAC™ inverted repeat sequences). These vectors may be useful in high throughput production of the modified barcoded transposon vectors described herein.

Other aspects of the present disclosure provide a population of cells and each cell comprises a transposon carrying a cargo element that comprises a promoter operably linked to a sequence encoding a transcription factor and a barcode that is located within 100 nucleotides (e.g., 50 nucleotides) of a terminator sequence. In some embodiments, the transposon comprises terminal repeats (e.g., inverted terminal repeat sequences or long terminal repeat sequences) flanking the cargo element. In some embodiments, the terminal repeats are recognized by a transposase (e.g., a piggyBAC™ transposase). In some embodiments, the nucleic acids encode more than one transcription factor and one barcode that uniquely identifies the combination of transcription factors encoded by the nucleic acid. In some embodiments, the cells further comprise a transposase. In some embodiments, the cell is a human cell. In some embodiments, the cell is a stem cell (e.g., an induced pluripotent stem cell).

Other aspects of the present disclosure provide methods that include introducing into cells (e.g., stem cells) a population of nucleic acids encoding a barcoded transcription factor expression transposon, detecting differences in gene expression in the cells to identify differentiated cells, and detecting at least one barcode to identify one or more transcription factors in the differentiated cells. In some embodiments, the cells comprise a transposase. In some embodiments, single cell RNA sequencing (e.g., droplet-based single cell RNA sequencing) is used to detect differences in gene expression. These methods may be used, for example, to analyze a library of transcription factors in an unbiased manner and identify combinations of transcription factors that induce stem cell differentiation.

BRIEF DESCRIPTION OF THE DRAWINGS

FIG. 1A shows a schematic of the piggyBAC™ expression vector without a barcode used in the initial transcription factor assay. Tet-On promoter refers to a doxycycline-inducible promoter. AttB1 and AttB2 are Gateway recombinase-based cloning sites. TF ORF refers to transcription factor open reading frame. V5 tag is a short protein epitope tag to verify protein expression. T refers to a transcriptional terminator. The first transcriptional terminator is the BGH (bovine growth hormone) terminator. The second transcriptional terminator is the SV40 (simian virus 40) terminator. EF1alpha is a constitutively active promoter. rtTA refers to a reverse tetracycline-controlled trans-activator. 2A is a self-cleaving peptide sequence that separates protein sequences. $Puro^R$ is a gene that confers puromycin resistance. The diagram is not to scale. FIG. 1B is a flowchart showing the experimental scheme of generating human induced pluripotent stem cells (hiPSCs) that overexpress TFs for single cell RNA sequencing. FIG. 1C is a pie chart showing the percentage of cells where the overexpressed TF could be detected (14.2%) compared to the percentage of cells where the overexpressed TF could not be detected (85.8%). FIG. 1D is a schematic depicting an example of individual sequencing reads that map to the vector in FIG. 1A. This diagram is to scale, 100 base pairs.

FIG. 4A is a schematic showing four regions of the piggyBAC™ vector considered for modification in the context of single cell RNA sequencing. NVT(30) refers to a random nucleotide (N), non-T base (V), 30 Ts T(30). FIG. 4B is a schematic showing design considerations within region 3 from FIG. 4A. FIG. 4C is a schematic showing a region with high sequence identity, which prevents specific primer binding. Sequences correspond to SEQ ID NOs: 31-32 from top to bottom. FIG. 4D is a schematic showing a repetitive region, which prevents accurate primer binding. The sequence corresponds to SEQ ID NO: 33. FIG. 4E is a schematic showing a region of high homopolymer content, which reduces amplification efficiency. The sequence corresponds to SEQ ID NO: 34.

FIG. 7A is a t-SNE projection showing single cell RNA-seq results for combinatorial TF assaying without reading out TF addresses. Single dots represent single cells. FIG. 7A shows that when TF addresses were not read out, many overexpressed TFs were not easily detected.. FIG. 7B is a t-SNE projection of single cell RNA-seq data for combinatorial TF assaying with address readout. FIG. 7B shows that a large number of cells in the top left cluster with TF overexpression was immediately detected when the TF addresses were read out. FIG. 7C is a t-SNE projection of a combination of differentiation and pluripotent cells by endogenous OCT4 expression. FIG. 7C shows that the rightmost cluster of single cells were likely hiPSCs that did not express TFs because they remained pluripotent as observed by the high OCT4 expression.

FIG. 8A is a schematic showing pDNOR shuttling vectors, each encoding one transcription factor (i.e., transcription factor 1 (TF1), transcription factor 2 (TF2) or transcription factor 3 (TF3)). FIG. 8B is a schematic showing PCR to add on a linker (squares) and AArI restriction sites (stars). FIG. 8C is a schematic showing digestion of the PCR products and the piggyBAC™ vector. FIG. 8D is a schematic showing ligation of the PCR products into the piggyBAC™ vector. FIG. 8E is a schematic showing a final piggyBAC™ vector encoding multiple transcription factors and a combination-specific barcode (address). Additional elements of the vector are labeled as in FIG. 5.

DETAILED DESCRIPTION

Figure 1:
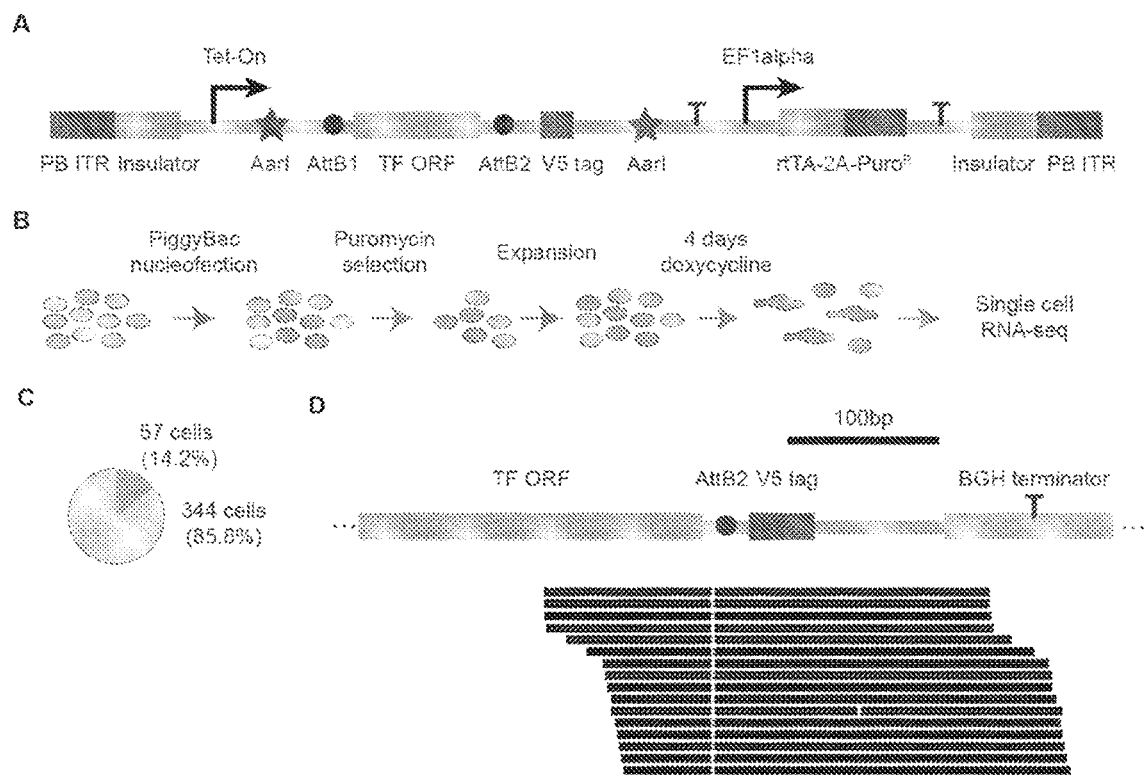
FIGS. 1A-1D include a series of schematics depicting a piggyBAC™ transcription factor (TF) expression vector that lacks a barcode and an initial transcription factor analysis in human induced pluripotent stem cells using this vector.

The technology described herein enables sensitive detection of combinatorial transcription factor expression in many (e.g., hundreds to thousands of) individual cells and mapping of transcription factor expression to a particular cell and/or cell type. The present disclosure is based, at least in part, on unexpected results demonstrating that a barcoded transposon vector, compatible with droplet-based single cell RNA sequencing, can be used in mammalian stem cells as an expression vector to identify, with high efficiency and accuracy, specific combinations of transcriptions factors that mediate cell type conversion processes.

Cells may be reprogrammed to produce a variety of cell types. For example, stem cells may be obtained from a patient, converted into a cell type that is suitable to improve a particular condition and reinfused into the patient. Such use of autologous cells minimizes the risk of an adverse immune response and enables personalized treatment. In order to promote cell type conversion (e.g., stem cell differentiation), however, it is necessary to identify a combination of transcription factors capable of cellular reprogramming. Existing methods, such as single cell RNA sequencing often cannot capture transcripts expressed from exogenous nucleic acids (i.e., nucleic acids introduced into cells) with high sensitivity. For example, single cell RNA sequencing may only identify a fraction of such transcripts. Thus, it is often necessary to filter out cells in which such transcripts cannot be detected and rely on a few cells with robust signal. Alternatively, transcriptomes from multiple cells can be pooled to increase detection, but such methods cannot be used in large-scale analyses to map particular transcription factor combinations with a specific transcriptome. The technology provided herein address the foregoing challenges.

The vectors of the present disclosure, in some embodiments, comprises a cargo element with (i) a promoter operably linked to a nucleotide sequence encoding a transcription factor and a barcode, and (ii) a terminator sequence, wherein the barcode, which uniquely identifies the transcription factor, is located within 100 nucleotides (e.g., within 95, within 90, within 80, within 75, within 70, within 65, within 60, within 55, within 50, within 45, within 40, within 35, within 30, within 25, within 20, within 15, within 10 or within 5 nucleotides) of the 5' end of the terminator sequence. In some embodiments, the cargo element is flanked by terminal repeat sequences (e.g., inverted terminal repeat sequences or long terminal repeat sequences) recognized by a cognate transposase. In some embodiments, the vector is a transposon vector (comprising a transposon).

Transposons

Transposons or transposable elements are mobile genetic elements that can insert into a nucleic acid. Structurally, a transposon comprises a cargo element (i.e., a nucleic acid sequence to be moved). Naturally-occurring transposons can move from one genomic locus to another. Transposons may comprise terminal repeat sequences (or terminal repeats), which are repetitive sequences flanking (on both ends of) a cargo sequences.

There are at least two classes of transposons. Class I transposons (also known as retrotransposons) are first transcribed into RNA, converted into DNA by reverse transcriptase and the resulting DNA is integrated into the genome at target sites. Class I transposons may be further classified into at least two subtypes. One subtype of class I transposons have long terminal repeats (repetitive sequences) flanking a cargo sequence while another subtype does not have long terminal repeat sequences. In contrast, class II transposons use a "cut and paste" mechanism, whereby the transposon is excised and inserted into a new location without an RNA intermediate. Class II transposons typically comprise a 5' inverted terminal repeat and a 3' inverted terminal repeat sequence flanking a cargo element. Inverted terminal repeats within a transposon are typically reverse complements of one another.

Transposases are enzymes that recognize the terminal repeats (e.g., long terminal repeats or inverted terminal repeats) on the ends of a transposon and catalyze the relocation of the transposon. For example, transposases can bind to terminal repeat sequences, excise the transposon carrying a cargo element, and insert the excised transposon into another nucleic acid.

Numerous transposon systems have been adapted for use in genetic engineering. For example, the piggyBAC™ transposon system was originally identified in the cabbage looper moth *Trichoplusia ni* (Fraser et al., J Virol. 1983; 47:287-300; Cary et al., Virology. 1989; 161:8-17). PiggyBAC™ transposases may bind to inverted terminal repeats comprising a TTAA sequence and transfer transposons into target sites comprising a TTAA sequence. An exemplary sequence encoding piggyBac™ transposase is described in GenBank accession number: EF587698. Other piggyBAC™ transposase sequences include piggyBAC™ variants (e.g., hyperactive piggyBAC™ transposase variants described in US 20130160152). The Sleeping Beauty transposon system was reconstructed from ancient fish genomes and are similar to the Tc1/mariner superfamily of transposons (Ivics et al., Cell. 1997 Nov. 14; 91(4):501-10). Sleeping Beauty transposases may insert transposons at target sites comprising a TA dinucleotide. Exemplary Sleeping Beauty transposases include transposases with wildtype sequence and variants thereof (e.g., SB11, SB100 and SB100X). See, e.g., Ivics et al., Cell. 1997 Nov. 14; 91(4):501-10 and Hou et al., Cancer Biol Ther. 2015; 16(1):8-16.

It should be understood that the present disclosure encompasses the use of any one or more of the transposases described herein as well as transposases that share a certain degree of sequence identity with the reference protein. The term "identity" refers to a relationship between the sequences of two or more polypeptides or polynucleotides, as determined by comparing the sequences. Identity measures the percent of identical matches between the smaller of two or more sequences with gap alignments (if any) addressed by a particular mathematical model or computer program (e.g., "algorithms"). Identity of related molecules can be readily calculated by known methods. "Percent (%) identity" as it applies to amino acid or nucleic acid sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Identity depends on a calculation of percent identity but may differ in value due to gaps and penalties introduced in the calculation. Variants of a particular sequence may have at least 70%, 75%, 80%, 85%, 90%, 91%, 92%, 93%, 94%, 95%, 96%, 97%, 98%, 99% but less than 100% sequence identity to that particular reference sequence, as determined by sequence alignment programs and parameters described herein and known to those skilled in the art.

The transposases described herein may contain one or more amino acid substitutions relative to its wild-type counterpart. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F.M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The comparison of sequences and determination of percent identity between two sequences can be accomplished using a mathematical algorithm. Techniques for determining identity are codified in publicly available computer programs. Exemplary computer software to determine homology between two sequences include, but are not limited to, GCG program package (Devereux, J. et al. Nucleic Acids Research, 12(1): 387, 1984), the BLAST suite (Altschul, S. F. et al. Nucleic Acids Res. 25: 3389, 1997), and FASTA (Altschul, S. F. et al. J. Molec. Biol. 215: 403, 1990). Other techniques include: the Smith-Waterman algorithm (Smith, T. F. et al. J. Mol. Biol. 147: 195, 1981; the Needleman-Wunsch algorithm (Needleman, S. B. et al. J. Mol. Biol. 48: 443, 1970; and the Fast Optimal Global Sequence Alignment Algorithm (FOGSAA) (Chakraborty, A. et al. Sci Rep.3: 1746, 2013).

Nucleic Acids and Cargo Elements

The nucleic acids of the present disclosure encode at least one transposon with a cargo element comprising a promoter operably linked to a nucleotide sequence encoding a transcription factor and a barcode that is located within 100 nucleotides 5' upstream of a terminator sequence.

In some embodiments, the nucleic acid comprises terminal repeat sequences (e.g., inverted terminal repeats or long terminal repeats) that are recognized by a transposase (e.g., piggyBAC™ transposase). A nucleic acid, generally, is at least two nucleotides covalently linked together, and in some instances, may contain phosphodiester bonds (e.g., a phosphodiester "backbone"). A nucleic acid is considered "engineered" if it does not occur in nature. As used herein, a population of nucleic acids indicates more than one nucleic acid (e.g., at least 2, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 1500, at least 2,000, at least 5,000 or at least 10,000 nucleic acids).

A terminator sequence is a nucleic acid sequence that mediates termination of transcription. Any terminator sequence known in the art or variants thereof may be used. For example, the terminator sequence may be a eukaryotic (e.g., mammalian) terminator sequence.

Exemplary mammalian terminator sequences include SV40 terminator sequences, hGH terminator sequences, BGH terminator sequences and rbGlob terminator sequences. In some embodiments, a terminator sequence comprises a AAUAAA sequence motif.

Barcodes

Each barcode is located within 100 nucleotides (e.g., within 95, within 90, within 80, within 75, within 70, within 65, within 60, within 55, within 50, within 45, within 40, within 35, within 30, within 25, within 20, within 15, within 10 or within 5 nucleotides) of a terminator sequence and is located 5' upstream of the terminator sequence. In some embodiments, the distance between the barcode and the 5' end of the terminator sequence permits detection of at least 50% (e.g., at least 60%, at least 70%, at least 80%, at least 90% or at least 99%) of cells comprising the barcode (e.g., as detected by single cell RNA sequencing).

A barcode may be 1-100 nucleotides in length (e.g., 1-10 nucleotides in length, 10-20 nucleotides in length, 20-30 nucleotides in length, 30-40 nucleotides in length, 40-50 nucleotides in length, 50-60 nucleotides in length, 60-70 nucleotides in length, 70-80 nucleotides in length or 90-100 nucleotides in length). A barcode may be 20-100 nucleotides in length. Any method known in the art may be used to generate the barcodes. See, e.g., Smith et al., Nucleic Acids Res. 2010 July; 38(13): e142 and the Examples section below.

The sequence of a particular barcode may have certain characteristics. In some embodiments, a barcode has 25-65% GC content. In some embodiments, a barcode a homopolymer sequence of up to four of the same base. In some embodiments, all the barcodes within a population of nucleic acids are unique. In some embodiments, each barcode within a population of nucleic acids has a Hamming distance of greater than or equal to 6. Any algorithm known in the art for calculating the Hamming distance may be used. Exemplary barcodes include, but are not limited to, those provided in Table 1. Other barcodes sequences may be generated and used as provided herein.

TABLE 1

Exemplary Barcode Sequences.

| Barcode Sequence | SEQ ID NO: |
| --- | --- |
| AAGTACGTTGTTTAGGAGTC | 1 |
| CGGAGTCATCGGAGAGAGCT | 2 |
| GTTTATGGATCACCCTAGGC | 3 |
| TAGAGCGTGGTCGTGAACAT | 4 |
| ACCTTACTGTGGTAGGTGAC | 5 |
| AGACTAGAGGATGCCCATCA | 6 |
| TGAGTACCAGTTATTAGCGG | 7 |
| TGCACTCCAGGTACTGAGTT | 8 |
| GCGTGTTCAAATGGTATAGG | 9 |
| ATACTGGATAGCCGATGTTT | 10 |

TABLE 1-continued

Exemplary Barcode Sequences.

| Barcode Sequence | SEQ ID NO: |
| --- | --- |
| CGTACCAATAACTCGAGGCA | 11 |
| TGGATAGGATGATGGTGAGC | 12 |
| TTGTGTCAGATTAGACAAGG | 13 |
| CCGGTGAAGAGGGAGTTTGC | 14 |
| CAGACCGTAAGGAGACTTTG | 15 |
| AATGGCAGGCCTTTGACATC | 16 |
| TTTCGAATTCGTTATTCTGA | 17 |
| CAAAGGAGGCGGTACTGAGC | 18 |
| TCGGGTGCAGAGTTCTTATA | 19 |

A barcode may uniquely identify at least one transcription factor (e.g., at least 2, at least 3, at least 4, at least 5, at least 10, at least 10, at least 20, at least 50 or at least 100 transcription factors). For example, one barcode sequence may be associated with one transcription factor among a particular population of transcription factors such that the sequence of the one barcode correlates with only that one transcription factor among the particular population of transcription factors. In some embodiments, a barcode uniquely identifies a combination of transcription factors (i.e., more than one transcription factor).

Any transcription factor from any species (e.g., human, mouse, dog, cat, pig or bird) known in the art and variants thereof may be used. The sequences of exemplary transcription factors may be obtained from the National Center for Biotechnology Information (NCBI) GenBank database. Exemplary transcription factors include, but are not limited to, those provided in Table 2. In some embodiments, the transcription factors direct stem cell differentiation or other cell type conversion process.

TABLE 2

Exemplary Transcription Factors.

| Transcription Factor | Exemplary GenBank Accession Number |
| --- | --- |
| ATOH1 | NP_005163.1 |
| NKX3-2 | NP_001180.1 |
| ETV2 | NP_001287903.1 |
| MYOG | NP_002470.2 |
| NEUROG3 | NP_066279.2 |
| FOXC1 | NP_001444.2 |
| SOX14 | NP_004180.1 |
| HOXB6 | NP_061825.2 |
| WT1 | NP_000369.4 |
| ZSCAN1 | NP_872378.3 |
| POU5F1 (OCT4) | NP_001167002.1 |
| SOX9 | NP_000337.1 |
| NKX6-1 | NP_006159.2 |
| NKX6-2 | NP_796374.1 |

Multicistronic Vectors

In some embodiments, a cargo element of the present disclosure comprises a promoter operably linked to a nucleotide sequence (e.g., open reading frame (ORF)) encoding at least one transcription factor (e.g., at least 2, at least 3, at least 4, at least 5, at least 10, at least 10, at least 20, at least 50 or at least 100 transcription factors) and a barcode located within 100 nucleotides (e.g., within 50 nucleotides) 5' upstream of a terminator. For example, for a cargo element encoding two or more transcription factors, each transcription factor may be operably linked to a different promoter or the same promoter. In some embodiments, a promoter is operably linked to at least two transcription factor nucleotide sequences (e.g., ORFs), wherein each transcription factor nucleotide sequence is separated by a separation sequence.

As used herein, a separation sequence promotes the formation of two separate amino acid sequences from one RNA transcript. For example, a separation sequence may encode a self-cleaving peptide. Exemplary self-cleaving peptides include 2A peptides (e.g., T2A, P2A, E2A and F2A). The sequence of 2A peptides and variants thereof are known in the art. An exemplary sequence for T2A is EGRGSLLTCGDVEENPGP (SEQ ID NO: 20), an exemplary sequence for P2A is ATNFSLLKQAGDVEENPGP (SEQ ID NO: 21), an exemplary sequence for E2A is QCTNYALLKLAGDVESNPGP (SEQ ID NO: 22) and an exemplary sequence for F2A is VKQTLNFDLLKLAGDVESNPGP (SEQ ID NO: 23). In some embodiments, a separation sequence is an internal ribosomal entry site elements (IRES) sequence.

Epitope Tags

The nucleotide sequence encoding the transcription factor and the barcode may further encode an epitope tag that enables detection of transcription factor expression. Exemplary epitope tags include c-Mc, V5, GFP, GST, FLAG and hemagglutinin A (HA). The epitope tag may be detected by assessing RNA or protein levels using any method known in the art (e.g., western blot, ELISA or reverse transcription polymerase chain reaction (RT-PCR)).

Selection Agents

The cargo elements of the present disclosure may further comprise a second promoter operably linked to a second nucleotide sequence encoding a selection marker and/or inducing agent in order to permit the selection of transcription factor-integrated cells and/or to control transcription. Selection markers include antibiotic resistance markers (e.g., puromycin, hygromycin or blasticidin) and fluorescent proteins (e.g., RFP, BFP, or GFP). Exemplary inducing agents include alcohols, tetracyclines (e.g., reverse tetracycline-controlled transactivator protein), steroids (e.g., estrogen), and metals. A separation sequence may be located in between a nucleotide sequence encoding a selection marker and a nucleotide sequence encoding an inducing agent. In some embodiments, an inducing agent is capable of promoting transcription from the promoter operably linked to a nucleotide sequence encoding a transcription factor and a barcode that is within 100 nucleotides 5' upstream of a terminator sequence.

Barrier insulator sequences known in the art may also be included in cargo elements to prevent chromatin silencing.

Promoters

A promoter control region of a nucleic acid is a sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

An inducible promoter is one that is characterized by initiating or enhancing transcriptional activity when in the presence of, influenced by or contacted by an inducing agent. An inducing agent may be endogenous or a normally exogenous condition, compound or protein that contacts an engineered nucleic acid in such a way as to be active in inducing transcriptional activity from the inducible promoter.

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, a nucleic acid comprises at least one inducible promoter (e.g., at least 2, at least 3, at least 4, at least 5, at least 6, at least, 8, or at least 10 inducible promoters). In some embodiments, a nucleic acid comprises an inducible promoter operably linked to a nucleotide sequence encoding a transcription factor and a barcode that is located within 100 nucleotides 5' upstream of a terminator sequence. In some embodiments, a nucleic acid comprises an inducible promoter operably linked to a nucleotide sequence encoding a selection marker and/or inducing agent.

A constitutive promoter is capable of initiating or enhancing transcriptional activity regardless of the presence or absence of an inducible agent. For example, a promoter may be a constitutive promoter suitable for expression within mammalian cells. Exemplary constitutive promoters include, but at are not limited to, EF1a, CMV, SV40, PGK1 and Ubc. In some embodiments, a nucleic acid comprises at least one constitutive promoter (e.g., at least 2, at least 3, at least 4, at least 5, at least 6, at least, 8, or at least 10 inducible promoters). In some embodiments, a nucleic acid comprises a constitutive promoter operably linked to a sequence encoding a selection marker or an inducing agent. In some embodiments, a nucleic acid comprises a constitutive promoter operably linked to a sequence encoding a transcription factor and a barcode that is located within 100 nucleotides 5' upstream of a terminator sequence.

Cloning Vectors

Some aspects of the present disclosure also provide cloning vectors for use, for example, in producing any of the nucleic acids described herein. In some embodiments, a cloning vector comprises a transposon in which the cargo element in the transposon comprises a promoter operably linked to a multiple cloning site and to a barcode that is located within 100 nucleotides (e.g., within 95, within 90, within 85, within 80, within 75, within 70, within 65, within 60, within 55, within 50, within 45, within 40, within 35, within 30, within 25, within 20, within 15, within 10 or within 5 nucleotides) 5' upstream of a terminator sequence. In some embodiments, the vector further comprises terminal repeats (e.g., inverted terminal repeats or long terminal repeats). The multiple cloning site may comprise at least two restriction enzyme recognition sites (e.g., AarI restriction enzyme sites). The cloning vector may be a piggyBAC™ cloning vector (i.e., a cloning vector with inverted piggy-BAC™ inverted terminal repeats).

Any of the nucleic acids and cloning vectors herein may be produced using any recombinant technique known in the art. In some embodiments, programmable restriction enzyme sites (e.g., AarI restriction enzyme sites) may be used to assemble a nucleic acid of the present disclosure. See, e.g., the Examples section below. In some embodiments, restriction sites recognized by different restriction enzymes are used to assemble a nucleic acid sequence encoding a combination of transcription factors in a predetermined order.

Methods and Cells

Provided herein are methods for identifying a combination of transcription factors capable of mediating cell differentiation. In some embodiments, the methods comprise contacting cells with a population of any of the nucleic acids described herein, identifying differentiated cells (e.g., using single cell RNA sequencing) and detecting one or more barcodes in the differentiated cells to identify the combination of transcription factors capable of inducing cell differentiation. In some embodiments, the cells further comprise a transposase.

Any of the nucleic acids may be introduced into cells (e.g., stem cells) using conventional methods (e.g., nucleofection) to express one or more transcription factors that may be identified by a barcode. A transposase may be delivered into cells using a separate expression vector encoding the transposase or the nucleic acids described herein may further encode a transposase. In some embodiments, a population of nucleic acids are introduced (e.g., by nucleofection) into cells such that cells receive at least one copy of any of the cargo elements described herein (e.g., at least 2, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 1500, at least 2,000, at least 5,000 or at least 10,000 cargo elements). For example, parameters including cell number, nucleic acid concentration, and transposase concentration may be altered for this purpose. See, e.g., the nucleofection conditions in the Examples section below. Cells may be further cultured in the presence of a selection agent (e.g., antibiotic) for at least one day (e.g., at least 2 days, at least 3 days, at least 3 days at least 5 days, at least 10 days or at least 14 days) to select for cells with genomic integration of a cargo element encoding a transcription factor. In some embodiments, cells are cultured in the presence of an inducing agent for at least one day (e.g., at least 2 days, at least 3 days, at least 3 days at least 5 days, at least 10 days or at least 14 days) to induce expression of one or more transcription factors.

Cell types may be characterized by their gene expression profiles. Therefore, gene expression at the RNA or protein level may be used to identify a particular cell type (e.g., to identify differentiated cells). For example, any single cell RNA sequencing technique known in the art (e.g., droplet-based single cell RNA sequencing) may be used to generate a gene expression profile of single cells and the transcriptome of a single cell may be mapped to a transcriptome of a known cell type. See, e.g., Klein et al., Cell. 2015 May 21;161(5):1187-1201. As an example, t-distributed stochastic neighbor embedded (t-SNE) may be used as a computational method to visualize single cell gene expression data. See, e.g., Maaten, J. Mach. Learn. Res. 2008; 9:2579-2605 for a description of t-SNE. The transcriptome may be used qualitatively or quantitatively. In some embodiments, single cell RNA sequencing is used to generate a gene expression profile (e.g., by assessing RNA expression of at least one gene) from a cell carrying any of the nucleic acids encoding a transcription factor of the present disclosure. This gene expression profile may then be compared with the gene expression profile of one or more control cells. Suitable control cells include cells that have not been contacted with a nucleic acid of the present disclosure. Control cells may be cells whose gene expression profile is associated with a particular cell type. Such comparison of gene expression profiles between single cells and cells of a known cell type may be used to identify single cells that are differentiated cells. Classification of transcription factor-induced lineages has previously been described. See e.g., International Patent Application Publication Number WO 2018/049382, which was published on Mar. 15, 2018. Additional methods for distinguishing between differentiated cells and non-differentiated cells include fluorescence activated cell sorting based on surface marker expression (e.g., expression of at least one lineage-specific cell surface antigen) and proteome analysis.

The barcode associated with a transcription or a combination of transcription factors may be detected using any sequencing method known in the art. In some embodiments, at least one barcode (e.g., at least 2, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 1500, at least 2,000, at least 5,000 or at least 10,000 barcodes) within a differentiated cell is detected. In some embodiments, RNA single cell sequencing is used to detect at least one barcode in a differentiated cell to identify at least one transcription factor.

In some embodiments, the methods described herein identify transcription factors capable of mediating stem cell differentiation. As used herein, a stem cell may be a pluripotent stem cell. Pluripotent stem cells are cells that have the capacity to self-renew by dividing, and to develop into the three primary germ cell layers of the early embryo, and therefore into all cells of the adult body, but not extra-embryonic tissues such as the placenta. Embryonic stem cells (ESCs) and induced pluripotent stem cells (iPSCs) are pluripotent stem cells. ESCs are derived from the undifferentiated inner mass cells of a human embryo and are able to differentiate into all derivatives of the three primary germ layers: ectoderm, endoderm and mesoderm. iPCSs can be generated directly from adult cells (Takahashi, K; Yamanaka, S. Cell 126(4):663-76, 2006). In some embodiments, a pluripotent stem cell is an ESC. In some embodiments, a pluripotent cell is an iPSC. In some embodiments, a pluripotent stem cell is a human ESC. In some embodiments, a pluripotent stem cell is an iPSC. In some embodiments, a pluripotent cell is a human iPSC. In some embodiments, a differentiated stem cell is a stem cell that has lost pluripotency.

A preparation of pluripotent stem cells (e.g., expressing the transcription factor combination as provided herein) may be cultured under standard stem cell culture conditions. For example, the pluripotent stem cells may be cultured in any commercially-available feeder-free maintenance medium for human ESCs and iPSCs, such as mTeSR™1 media. In some embodiments, the pluripotent stem cells are cultured in commercially-available stem cell media without added nutrients or growth factors.

Differentiated cells may be separated from stem cells by gene expression (e.g., RNA or protein expression) as described above. For example, expression of markers, including TRA-1-60, OCT4 or a combination thereof, may be used to distinguish pluripotent cells from differentiated cells. See, e.g., the Examples section below and International Patent Application Publication Number WO 2018/049382, which was published on Mar. 15, 2018.

Aspects of the present disclosure also provide a cell, including a population of cells, comprising any of the nucleic acids described herein. In some embodiments, the cell further comprise a transposase.

Examples

Example 1: Development of a Barcoded piggyBAC™ Transcription Factor Expression Vector Suitable for Single-Cell Sequencing To first pilot a combinatorial transcription factor (TF) assay using single cell RNA-sequencing, a piggyBAC™ expression vector without a barcode was used (FIG. 1A). The piggyBAC™ vector containing TFs was nucleofected into human induced pluripotent stem cells (hiPSCs), puromycin selection was performed to isolate cells that have stably integrated the TFs, and these cells were expanded and TF overexpression was induced by doxycycline addition for four days (FIG. 1B). Emulsion-droplet-based RNA sequencing, which captures single cells within aqueous droplets containing a barcoded gel with a unique cell barcode (Klein et al., Cell 161, 1187-1201 (2015); Macosko et al., Cell 161, 1202-1214 (2015)), was performed. Libraries were prepared and 401 single cells were sequenced. The overexpressed TFs were detected and identified in only 57 of 401 cells (14.2%, FIG. 1C). Furthermore, for cells where any signal of the overexpressed TF was detected, the TF ORF could not be identified because too few bases were sequenced, likely due to fragmentation of upstream sequence (FIG. 1D). Thus, these results demonstrate two issues: first, the overexpressed TF could not be detected in a sensitive manner in most cells and second, of the TFs detected, it was not possible to reliably identify it.

Figure 2:
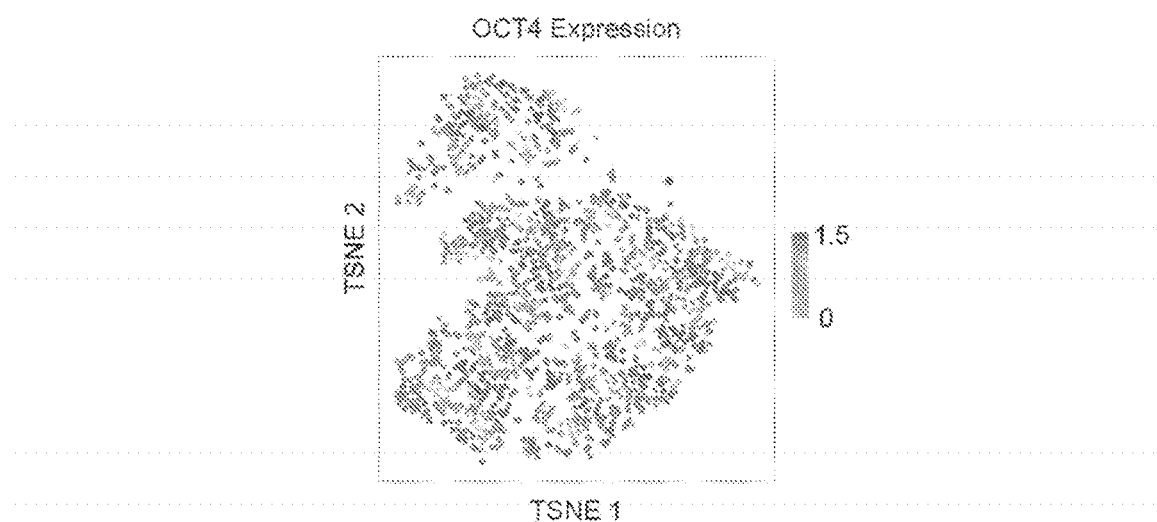
FIG. 2 is a t-distributed stochastic neighbor embedded (t-SNE) projection of single cell RNA-sequencing results of human induced pluripotent stem cells (hiPSCs) without TF overexpression and shows expression of the endogenous, lowly expressed OCT4 TF. Each dot is a single cell. This pluripotency TF is expressed at low levels in cells, yet robust expression of this TF was detected in virtually all cells without modification to the protocol

To improve sensitivity of detection and identification of the overexpressed TF, improvements in the reverse transcription step were tested. Single cell RNA-seq was performed on hiPSCs without TF overexpression and expression of an endogenous TF, OCT4, was assessed. This pluripotency TF is expressed at low levels in cells, yet robust expression of this TF was detected in virtually all cells without modification to the protocol (FIG. 2). This suggested that adaptations in reverse transcription or library preparation may not yield large gains in signal.

Figure 3:
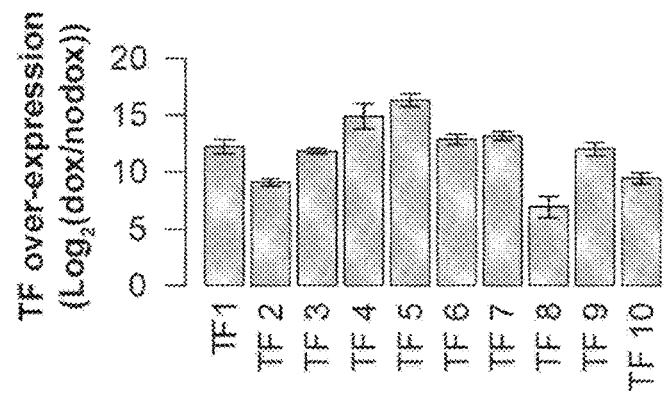
FIG. 3 is a chart showing analysis of TF overexpression using population RNA sequencing. Error bars show standard errors of the mean. The transcription factors used were as follows: TF1=ATOH1, TF 2=NKX3-2, TF 3=ETV2, TF 4=MYOG, TF 5=NEUROG3, TF 6=FOXC1, TF 7=SOX14, TF 8=HOXB6, TF 9=WT1 and TF 10=ZSCAN1.

To test whether improvements to the expression level of the overexpressed TF itself boost detection levels, the RNA-seq experiments were analyzed to determine the level of overexpression of the TFs. Robust expression of the overexpressed TF was observed, with levels up to an increase of 30,000-fold compared to non-induced controls (FIG. 3). Due to the high level of overexpression, it was concluded that it is not advantageous to further maximize overexpression, as this may already be at maximal levels and further increases could affect cell physiology, for instance by reducing available ribosomes for the production of essential proteins.

Based on the observations that single cell RNA sequencing could detect endogenous, TF expression at low levels and exogenous overexpression at high levels, a new vector was rationally designed to enable detection and identification of the TFs overexpressed at high levels (FIGS. 4A-4E).

Figure 4:
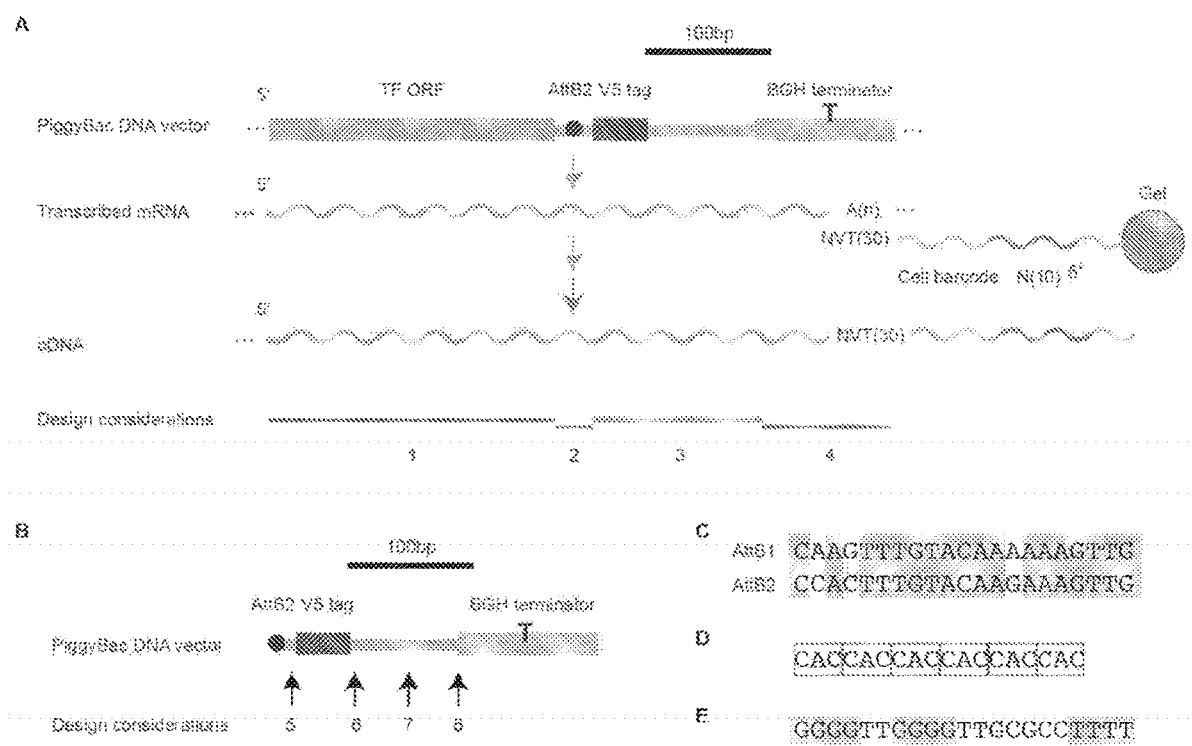
FIGS. 4A-4E include a series of schematics showing design considerations for modifications in the piggyBAC™ vector.

First, the location of modifications that would minimize impact to the function of the vector, while being compatible with single cell RNA sequencing, were considered. This was viewed in light of the library preparation process (FIG. 4A). Modifications in sequence region 1 may cause changes in TF function. Modifications in sequence region 2 may inhibit cloning of the TF into the vector. Modifications in sequence region 3 may be possible. Modifications in sequence region 4 may adversely affect transcriptional termination. For these reasons, engineering improvements were focused on sequence region 3.

Figure 5:
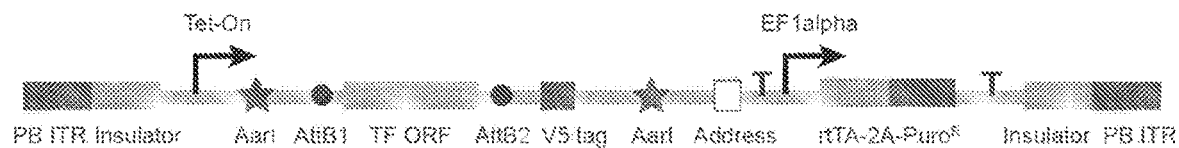
FIG. 5 is a schematic showing a barcoded piggyBAC™ transcription factor expression vector. The location of the barcode is indicated as "address." The elements of the vector are indicated as follows: ITR=5' and 3' piggyBAC™ inverted terminal repeats for integration into the genome, AttB1 and AttB2=Gateway recombinase-based cloning sites, Insulator=Transcriptional insulator sequence to prevent chromatin silencing, Tet-On=doxycycline-inducible promoter, TF=transcription factor open reading frame; AarI=AarI restriction enzyme recognition site, 2A=2A cleaving peptide, Address=TF-specific barcode for single cell RNA-seq readout, T=transcriptional terminator, EFlalpha=constitutively active promoter, rtTA=reverse tetracycline trans-activator and $Puro^R$=puromycin resistance gene.

Sequence region 3 contains 143 base pairs. This region was further analyzed to determine areas that were amenable to modification (FIG. 4B). Modifications to sequence region 5 used a primer upstream for PCR. Such a primer would bind AttB2. However, this region had high sequence identity with another region on the vector, AttB1 (FIG. 4C). This prevented specific primer binding. Next, sequence region 6 was considered. The upstream primer would bind the V5 tag, which had previously been used successfully for PCR. However, based on the experiments described in FIG. 1, these bases were far away from the transcriptional terminator, and hence the capture site near the gel. This meant this area could not be sequenced due to fragmentation. Therefore, sequence region 7 was considered, which was closer to the capture site near the gel. However, repetitive sequences (FIG. 4D) and sequences with high homopolymer content (FIG. 4E) were found. For these reasons, sequence region 8 was determined to be ideal for modification. A schematic of a barcoded piggyBAC™ vector for transcription factor expression is provided in FIG. 5. The barcode (i.e.: address) is located upstream of the first transcription terminator sequence (indicated by a bolded T in FIG. 5). This transcription factor expression vector enables targeted detection of the barcode, which is directly linked to the transcription factor.

Figure 6:
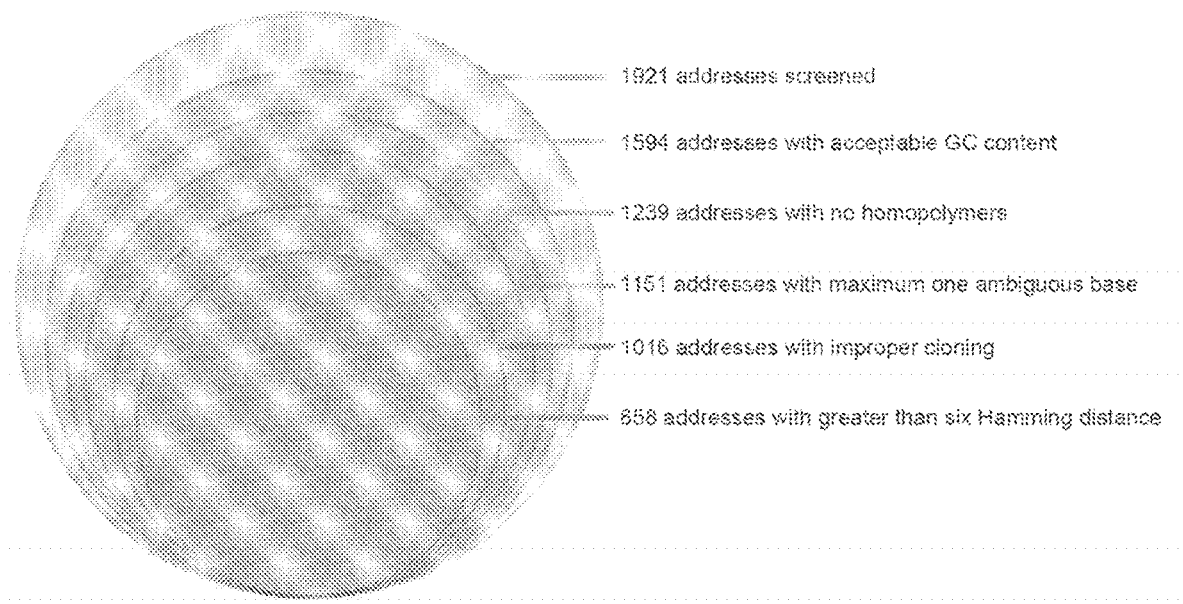
FIG. 6 is a schematic showing assaying of TF-specific addresses (barcodes).

With a suitable sequence region identified, TF-specific DNA addresses (barcodes) were cloned into sequence region 8 of the piggyBAC™ vector that could be recovered by single cell RNA sequencing. 1,921 addresses were cloned and assayed for additional features that would maximize the sensitivity of detection, to arrive at 858 high-quality addresses (FIG. 6). First, addresses outside a 25-65% GC content were rejected, resulting in 1,594 acceptable addresses.

Then, addresses with homopolymers of greater than four of the same base were removed, resulting 1,239 addresses. Additionally, addresses where more than one base was ambiguous were removed, yielding 1,151 addresses. Another set of addresses were rejected due to improper cloning and 1,016 addresses passed. Finally, all addresses were compared to every other address to remove those that were similar, as defined by a Hamming distance of less than 6. This resulted in 858 acceptable addresses.

Figure 7:
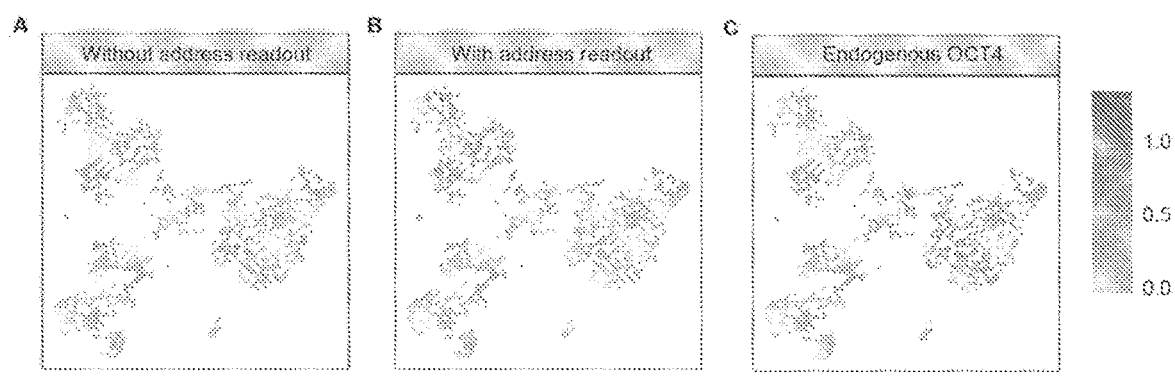
FIGS. 7A-7C include a series of t-SNE projections showing single cell RNA-seq results with or without amplifying the TF addresses (barcodes).

With this TF-addressable (TF-barcoded) piggyBAC™ vector, detection of the overexpressed TF was tested by single cell RNA sequencing. A new population of hiPSCs was generated containing a combination of TFs expressed using this new, single-cell optimized piggyBAC™ vector, and mixed it with a population of hiPSCs containing TFs expressed using the original piggyBAC™ vector for comparison and with a population of hiPSCs that did not express TFs as a negative control. The combination of TFs used were neurogenin-3 (NGN3), NKX3.2 and ETV2 and each transcription factor was delivered on a separate barcoded piggyBAC™ vector. Single cell RNA-seq with or without amplifying the TF addresses was performed. The three populations of cells could immediately be identified by single cell RNA sequencing, as three clusters appeared using t-SNE projection (FIGS. 7A-7C). When TF addresses were not read out, many overexpressed TFs were not easily detected (FIG. 7A). In contrast, using the optimized detection by reading out the TF address, a large number of cells in the top left cluster with TF overexpression was immediately detected (FIG. 7B). This was not seen in the other two clusters, as expected, due to the lack of these addresses or the lack of TFs. It was possible to infer that the rightmost cluster were hiPSCs that did not express TFs because they remained pluripotent as observed by the high OCT4 expression (FIG. 7C). Together, these results demonstrate an ability to simultaneously detect changes in the transcriptomic state of single cells as well as the overexpressed TFs that caused this change.

Methods

Cell Culture

The PGP1 hiPSC line without genomically integrated Yamanaka factors was generated from fibroblasts (Coriell, GM23248) (72) using the CytoTune Sendai Reprogramming Kit (Life Tech, A16517). They were adapted to feeder-free culture, verified for pluripotency by FACS, and karyotyped. Cell lines were verified by short tandem repeat (STR) profiling (Dana Farber Cancer Institute), regularly verified to be mycoplasma-free using PlasmoTest (InvivoGen, rep-ptl), and cultured between passages 8 and 40. hiPSCs were cultured in mTeSR1 (STEMCELL Technologies, 05850) without antibiotics on tissue-culture-treated plates coated with Matrigel (Corning, 354277). hiPSCs were passaged using TrypLE Express (Life Technologies, 12604013) and seeded with 10 µM Y-27632 ROCK inhibitor (Millipore, 688001) for one day. Cells were frozen in mFreSR (STEMCELL Technologies, 5854) using a CoolCell LX (Biocision, BCS-405) overnight at −80° C., then in vapor-phase liquid nitrogen for long-term storage.

Nucleofection of piggyBAC™ and Generation of Stable Cell Lines

The first piggyBAC™ vector without a barcode, PBAN is a Gateway-compatible, doxycycline-inducible, puromycin-selectable piggyBAC™ vector. It was constructed from PB-TRE-dCas9-VPR (Addgene #63800). Individual pDONR-TFs were cloned into PBAN using LR Clonase II. 500,000 to 800,000 hiPSCs were nucleofected with PBAN-TF and Super piggyBAC™ Transposase (SPB; System Biosciences, PB210PA-1) at a DNA ratio of 4:1 using Nucleofector P3 solution (Lonza, V4XP-3032). Nucleofected cells were transferred to a 6-well Matrigel-coated plate in mTeSR1 with ROCK inhibitor. When cells reached 80% confluence, 1 pg/ml puromycin (Gibco, A1113803) was added. The next day, dead cells in suspension were washed away using PBS; if the remaining cells were sparse, ROCK inhibitor was added to prevent colony collapse. 500 ng/mL doxycycline (Sigma) was used for induction.

Droplet-Based Single Cell RNA-Seq Library Preparation and Analysis

Cells were dissociated, counted and resuspended in mTeSR1 and captured with the droplet-based Chromium V2 single cell RNA-seq kit (10× Genomics, 120237) using manufacturer's protocols. Libraries were sequenced on an Illumina MiSeq or NextSeq, and processed using 10× Genomics' CellRanger pipeline to generate gene-cell barcode-matrices. To readout TF addresses, 10 ng of the sample after whole-transcriptome amplification was used for PCR using universal address primers to amplify the addresses with Illumina sequencing adaptors.

Forward primer:
(SEQ ID NO: 24)
5'-AATGATACGGCGACCACCGAGATCTACACTCTTTCCCTACACGACGC

TC

Reverse primers (unique to each sample):
(SEQ ID NO: 25)
5'-CAAGCAGAAGACGGCATACGAGATatgctgtcGTGACTGGAGTTCAG

ACGTGTGCTCTTCCGATCTCCAAGCACCTGCTACATAGC (SEQ ID NO: 26)
5'-CAAGCAGAAGACGGCATACGAGATtgtacaaaGTGACTGGAGTTCAG

ACGTGTGCTCTTCCGATCTCCAAGCACCTGCTACATAGC (SEQ ID NO: 27)
5'-CAAGCAGAAGACGGCATACGAGATcacggcctGTGACTGGAGTTCAG

ACGTGTGCTCTTCCGATCTCCAAGCACCTGCTACATAGC (SEQ ID NO: 28)
5'-CAAGCAGAAGACGGCATACGAGATgcatatggGTGACGGGTATTCAG

ACGTGTGCTCTTCCGATCTCCAAGCACCTGCTACATAGC (SEQ ID NO: 29)
5'-CAAGCAGAAGACGGCATACGAGATtactcgccGTGACTGGAGTTCAG

ACGTGTGCTCTTCCGATCTCCAAGCACCTGCTACATAGC (SEQ ID NO: 30)
5'-CAAGCAGAAGACGGCATACGAGATatagaagtGTGACTGGAGTTCAG

ACGTGTGCTCTTCCGATCTCCAAGCACCTGCTACATAGC

Amplified addresses were sequenced on an Illumina MiSeq. The sequencing data was processing using custom perl scripts that extracted the TF addresses belonging to each cell to assign counts.

Single cell sequencing data was visualized in Geneious as raw sequencing reads, or in R as t-SNE plots.

Comparison with Population RNA Sequencing: Library Preparation

600 µl TRIzol (Life Technologies, 15596-018) was added directly to cells, which were then incubated for 3 minutes and used for RNA extraction using Direct-zol RNA Mini-Prep (Zymo Research, R2050). At least three replicates of control cells (without doxycycline) were processed in parallel in each set of library preps. RNA was quantified using Qubit RNA HS Kit (Molecular Probes, Q32852) and RNA integrity was confirmed by the presence of intact 18S and 28S bands on a 1% E-Gel EX. 1 µg RNA was used for Poly(A) isolation using the NEBNext Poly(A) mRNA Magnetic Isolation Module (New England Biolabs, E7490L) and the NEBNext Ultra Directional RNA Library Prep Kit for Illumina (New England Biolabs, E7420L). To prevent library over-amplification, one-fifth of the PCR reaction was amplified by quantitative PCR using SYBR Gold Nucleic Acid Statin on a Roche Lightcycler 480. The remaining reaction was amplified using the number of cycles needed to reach mid-log amplification. Library size was visualized on a 1% E-Gel EX, and quantified using KAPA Library Quantification Kit as described before.

Analysis of Population RNA Sequencing Data.

A STAR human transcriptome reference index was generated using Gencode GRCh38.primary: (ftp://ftp.sanger.ac.uk/pub/gencode/Gencode_human/release_25/GRCh38.primary_assembly.gen ome.fa.gz) as the genome sequence and Gencode v25 transcript annotations (ftp://ftp.sanger.ac.uk/pub/gencode/Gencode_human/release_25/gencode.v25. annotation.gtf.gz). RNA-seq reads were aligned on four codes each with 12 Gb memory using the command: STAR-quanode GeneCounts.

Gene counts per sample were merged into a master table and analyzed in R version 3.2.2. Differential expression analysis was performed using DESeq 2 (73), comparing each batch to its no-doxycycline control separately. FASTQ files will be available on NCBI GEO.

Construction of piggyBAC™ Vector for TF Addressable Readout Using Single Cell RNA Addresses were synthesized as primers (Integrated DNA Technologies) and PCR using HiFi HotStart (KAPA Biosystems) was used to construct double stranded DNA fragments. These fragments were cloned into the first generation piggyBAC™ PBAN vector described above upstream of BGH transcriptional terminator. Single colonies were sequenced and assayed for acceptable addresses by Sanger sequencing, and re-arrayed into individually addressable 96-well plates. Specific TFs were Gateway cloned into these individually addressed piggyBAC™ vectors using LR clonase (Invitrogen), and used to create stable hiPSC lines.

Figure 8:
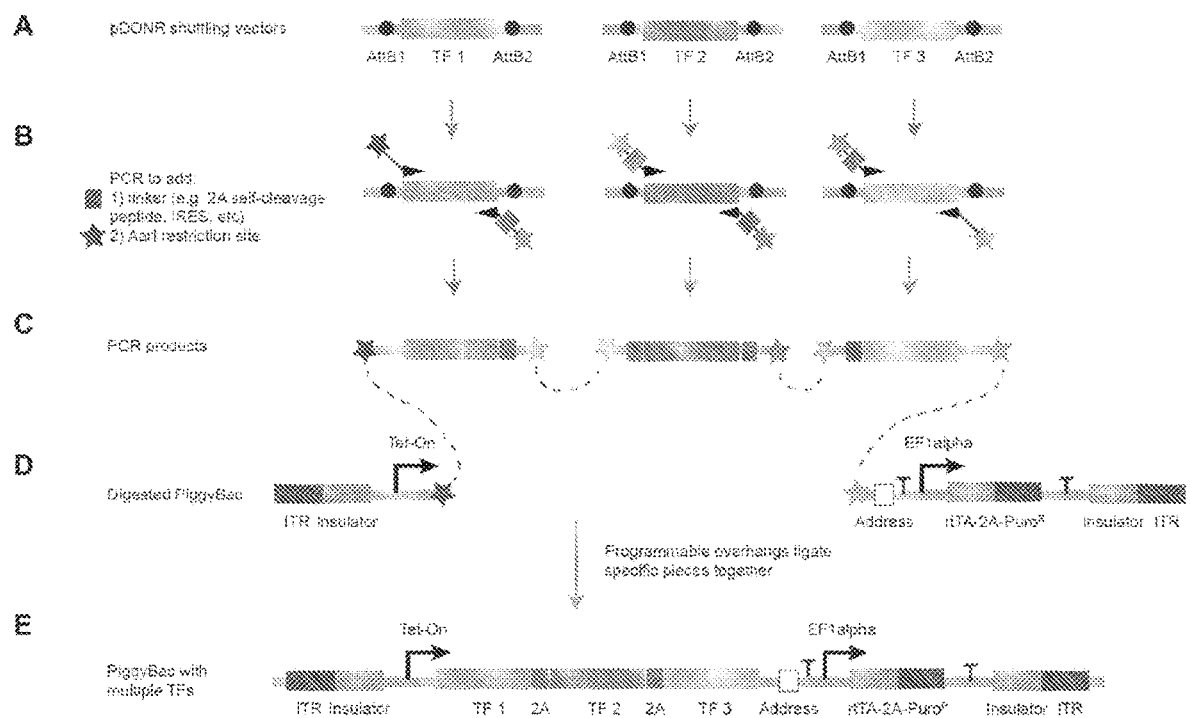
FIGS. 8A-8E is a series of schematics depicting assembly of multiple transcription factors into one barcoded piggyBAC™ vector using programmable AarI restriction enzyme sites.

Example 2: A Barcoded piggyBAC™ Vector Encoding Multiple Transcription Factors FIGS. 8A-8E show steps for cloning of a barcoded piggyBAC™ vector encoding multiple transcription factors. PDNOR shuttle vectors with an open reading frame encoding with each of the transcription factors (FIG. 8A) may be used. Polymerase chain reaction may be used to add a linker (e.g., encoding 2A self-cleavage peptide, IRES, etc.) between each of the open reading frames and to add AarI restriction sites flanking each open reading frame (FIG. 8B). The PCR products and the piggyBAC™ vector may be digested with the AarI restriction enzyme (FIG. 8C) to generate programmable overhangs. The digested PCR products and vector can then be ligated together (FIG. 8D) to produce the final barcoded vector encoding multiple transcription factors (FIG. 8E).

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

---

What is claimed is:

1. A method of identifying at least one transcription factor, comprising:
    (a) contacting cells that comprise a transposase with a population of nucleic acids, wherein each nucleic acid comprises a cargo element flanked by terminal repeat sequences that are recognized by the transposase, wherein each cargo element comprises
        (i) a first promoter operably linked to a first nucleotide sequence encoding a transcription factor and a barcode, and
        (ii) a terminator having a 5' end,
    wherein the barcode uniquely identifies the transcription factor and is located within 100 nucleotides of the 5' end of the terminator;
    (b) detecting differences in gene expression in the cells compared to control cells and identifying differentiated cells, wherein the differentiated cells have decreased expression of one or more stem cell markers compared to control cells; and
    (d) detecting one or more barcodes in the differentiated cells and identifying a transcription factor or a combination of transcription factors in the differentiated cells.

2. The method of claim 1, wherein the barcode is located within 50 nucleotides of the 5' end of the terminator.

3. The method of claim 1, wherein the terminal repeat sequences are inverted terminal repeat sequences.

4. The method of claim 1, wherein each nucleic acid further comprises a second promoter operably linked to a second nucleotide sequence encoding a selection marker.

5. The method of claim 1, wherein each nucleic acid further comprises a second promoter operably linked to a second nucleotide sequence encoding an inducing agent.

6. The method of claim 5, further comprising contacting cells with an inducing agent.

7. The method of claim 1, wherein each nucleic acid further comprises a second promoter operably linked to a second nucleotide sequence encoding a selection marker and an inducing agent.

8. The method of claim 1, wherein the first nucleotide sequence further encodes an epitope tag.

9. The method of claim 1, wherein the barcode has a length of 20-100 nucleotides.

10. The method of claim 1, wherein the control cells are not contacted with the plurality of nucleic acids.

11. The method of claim 1, further comprising selecting cells with a selection agent.

12. The method of claim 1, wherein the cargo element further comprises barrier insulator sequences.

13. The method of claim 1, wherein the cells are human cells.

14. The method of claim 1, wherein the cells are stem cells, optionally induced pluripotent stem cells.

15. The method of claim 1, wherein the detecting step (b) comprises using single cell RNA sequencing to detect differences in gene expression in the cells compared to control cells to identify differentiated cells.

16. The method of claim 1, wherein the first nucleotide sequence encodes at least two transcription factors.

17. A population of nucleic acids, wherein each nucleic acid comprises a cargo element flanked by terminal repeat sequences that are recognized by a transposase,
    wherein the cargo element of each nucleic acid comprises:
    (a) a first promoter operably linked to a first nucleotide sequence encoding at least one transcription factor and a barcode; and
    (b) a terminator, and
    wherein the barcode uniquely identifies the transcription factor and is located within 100 nucleotides of the 5' end of the terminator.

18. The population of nucleic acids of claim 17, wherein the terminal repeat sequences are inverted terminal repeat sequences.

19. The population of nucleic acids of claim 17, wherein each nucleic acid further comprises a second promoter operably linked to a second nucleotide sequence encoding a selection marker.

20. The population of nucleic acids of claim 17, wherein each nucleic acid further comprises a second promoter operably linked to a second nucleotide sequence encoding an inducing agent.

21. The population of nucleic acids of claim 17, wherein each nucleic acid further comprises a second promoter operably linked to a second nucleotide sequence encoding a selection marker and an inducing agent.

22. The population of nucleic acids of claim 17, wherein the first nucleotide sequence further encodes an epitope tag.

23. The population of nucleic acids of claim 17, wherein the barcode has a length of 20-100 nucleotides.

24. The population of nucleic acids of claim 17, wherein the cargo element further comprises barrier insulator sequences.

25. The population of nucleic acids of claim 17, wherein the first nucleotide sequence encodes at least two transcription factors.

26. A population of cells, wherein each cell comprises a transposase and a nucleic acid that comprises a cargo element flanked by terminal repeat sequences that are recognized by a transposase,
    wherein the cargo element of each nucleic acid comprises:
    (a) a first promoter operably linked to a first nucleotide sequence encoding at least one transcription factor and a barcode; and
    (b) a terminator, and
    wherein the barcode uniquely identifies the transcription factor and is located within 100 nucleotides of the 5' end of the terminator.

27. The population of cells of claim 26, wherein the terminal repeat sequences are inverted terminal repeat sequences.

28. The population of cells of claim 26, wherein each nucleic acid further comprises a second promoter operably linked to a second nucleotide sequence encoding a selection marker.

29. The population of cells of claim 26, wherein each nucleic acid further comprises a second promoter operably linked to a second nucleotide sequence encoding an inducing agent.

30. The population of cells of claim 26, wherein each nucleic acid further comprises a second promoter operably linked to a second nucleotide sequence encoding a selection marker and an inducing agent.

31. The population of cells of claim 26, wherein the first nucleotide sequence further encodes an epitope tag.

32. The population of cells of claim 26, wherein the barcode has a length of 20-100 nucleotides.

33. The population of cells of claim 26, wherein the cargo element further comprises barrier insulator sequences.

34. The population of cells of claim 26, wherein the cells are human cells.

35. The population of cells of claim 26, wherein the cells are stem cells, optionally induced pluripotent stem cells.

36. The population of cells of claim 26, wherein the first nucleotide sequence encodes at least two transcription factors.

* * * * *